(12) United States Patent
Frank et al.

(10) Patent No.: US 7,114,392 B2
(45) Date of Patent: Oct. 3, 2006

(54) METHOD OF ANALYZING GRANULAR COMPOSITION BY ACOUSTIC EMISSION

(75) Inventors: Ragnhild Frank, Roskilde (DK); Peter Paasch Mortensen, Kalundborg (DK)

(73) Assignee: Novozymes A/S, Bagsvaerd (DK)

( * ) Notice: Subject to any disclaimer, the term of this patent is extended or adjusted under 35 U.S.C. 154(b) by 314 days.

(21) Appl. No.: 10/092,877

(22) Filed: Mar. 7, 2002

(65) Prior Publication Data

US 2002/0189358 A1 Dec. 19, 2002

Related U.S. Application Data

(60) Provisional application No. 60/277,777, filed on Mar. 21, 2001.

(30) Foreign Application Priority Data

Mar. 8, 2001 (DK) ........................ 2001 00380

(51) Int. Cl.
  G01N 15/02 (2006.01)
  G01H 17/00 (2006.01)

(52) U.S. Cl. .......................................... 73/579; 73/587

(58) Field of Classification Search ............ 73/587, 73/602, 579
  See application file for complete search history.

(56) References Cited

U.S. PATENT DOCUMENTS 4,024,768 A * 5/1977 Leach et al. ............... 73/865.5
4,283,953 A    8/1981 Plona ......................... 73/589
5,022,266 A * 6/1991 Cody et al. .................. 73/579
5,040,734 A * 8/1991 Belchamber et al. ......... 241/30
5,648,610 A * 7/1997 Laine et al. ................. 73/587
6,035,716 A * 3/2000 Beekman et al. ............ 73/579

FOREIGN PATENT DOCUMENTS

JP    7-246326    *  9/1995

OTHER PUBLICATIONS

Tsujimoto et al., Powder Technology, vol. 113, p. 88–96 (2000).

Esbensen et al., Chemometrics and Intelligent Laboratory Systems vol. 44, p. 61–76 (1998).

Whitaker et al., International Journal of Pharmaceuticals, vol. 205, p. 79–91, (2000).

* cited by examiner

*Primary Examiner*—Helen Kwok
*Assistant Examiner*—Rose M. Miller
(74) *Attorney, Agent, or Firm*—Jason Garbell; Elias Lambiris (57) ABSTRACT

The present invention relates to a method for acoustic emission analysis of a granular composition comprising a biologically active compound, said method comprising colliding the granular composition with at least one surface transmitting low frequency vibrations, recording low frequency vibration data in range of 10 Hz to less than 50 kHz, arising from the collision, with at least one vibration detector and subjecting the recorded low frequency vibration data to computerized data processing.

19 Claims, 5 Drawing Sheets

METHOD OF ANALYZING GRANULAR COMPOSITION BY ACOUSTIC EMISSION

CROSS-REFERENCE TO RELATED APPLICATIONS

This application claims priority from Danish Patent Application No. PA 2001 00380 and the benefit of U.S. provisional application No. 60/277,777, filed Mar. 21, 2001 the contents of which are fully incorporated herein by reference.

FIELD OF THE INVENTION

The present invention relates to a method for determining properties of a granular composition comprising an active compound by subjecting the granular composition to acoustic emission analysis. The invention also relates to a method for producing a granular composition comprising subjecting the granular composition to acoustic emission analysis. Further the invention relates to a granulation and/or coating apparatus suitable for preparing a granular composition comprising an active compound said apparatus comprising means for performing acoustic emission analysis.

BACKGROUND OF THE INVENTION

Acoustic emission methods are, inter alia, known from Whitaker et al. Application of acoustic emission to the monitoring and end point determination of a high shear granulation process, Int. J. Pharm., 205, pp 79–91, 2000. Methods of using acoustic emission analysis e.g. on sand powders are known from Esbensen K. et al, Acoustic chemometrics—from noise to information, Chemometrics and intelligent laboratory systems, 44 (1998) 61–76. Methods of using high frequency acoustic emission analysis in fluid beds are known from Tsujimoto H. et al, Monitoring particle fluidization in a fluidized bed granulator with an acoustic emission sensor, Powder technology, 113 (2000) 88–96.

SUMMARY OF THE INVENTION

The present invention relates to a method for analyzing a property of a granular composition and/or granules comprising a biologically active compound by subjecting the granular composition to acoustic emission analysis. Formulation of chemical compounds into finished goods, in particular granulation, is usually required to achieve improved properties of the products, thus making them more commercially attractive. However, for biologically active compounds, granulation is often compulsory to the producers because the active compound must, until being applied in the intentional use, be separated from the surrounding environment to ensure the safe handling of the product. The amount of biologically active compound which can escape from the granulated product, e.g. in the form of dust, must be minimized to ensure that persons handling the product do not suffer any adverse effects from contact with the biologically active compound. Vice versa the active compound must be protected from the environment outside the granule to remain stabile and active until it is to be used. Once an active compound has been granulated it is known that one may further coat granules comprising biologically active compound with a coating agent which further suppress the release of active compound from the granule and further improve the stability of the active compound in the granule.

During the granulation process, fluctuations in physical and chemical process conditions e.g. temperature, composition, mixing power, may appear and cause process instability. This instability in the granulation process may result in granular compositions falling outside the expected properties.

One object of the invention is, to provide methods for detecting, and/or predicting in a granular composition comprising a biologically active compound, a quality parameter of the granular composition such as the amount of active compound released from granules in the form of active dust, during or after the process for preparing the granular composition and/or particle size distribution of the granules and/or stickiness/tackiness of the granules and/or moisture content of the granules and/or dryness of the granules and/or shape of the granules and/or thickness and/or integrity of coating layers applied to the granules to suppress dust formation and increase the stability of the active compound etc. A second object of the invention is to provide, in a process for preparing a granular composition comprising a biologically active compound means for controlling one or more quality parameters and providing means for correcting the process if one or more quality parameters are outside a desired range.

More specifically one object of the invention is to design a granulation apparatus and to select method setup, so that the method of acoustic emission analysis may be used on-line or in-line in the production of such granular compositions, and that the methods of the invention in real time may provide information about levels of dust comprising biologically active compound during processing of the granular composition. A further object of the invention is to provide a useful method of controlling the production of enzyme containing granules/granulates in large industrial scale.

We have found that in the process control in the making of granular compositions comprising a biologically active compound not only the quality of granules formed may by evaluated also the amount of small dust particles present in the granular composition e.g. as a result from release of dust from the granules or as a result from insufficient granulation can be evaluated by recording sound and/or vibration signals arising from granules and dust of the granular composition interacting or colliding with the granulator walls and subjecting the recorded vibration signals to computerized data processing.

Furthermore, using the present invention we have found that in the process control of the making of granular compositions comprising a biologically active compound we can, if any of the quality parameters or properties of the granular composition such as the above mentioned quality parameters are outside a desired range, by recording vibration signals arising from the granular composition interacting and colliding with the granulator walls and subjecting the recorded vibration signals to computerized data processing, change one or more process conditions either manually or through an automated system to restore the quality parameter into the desired range. The process condition to be changed may be any parameter influencing the granulation process and/or the properties of the formed granules.

We also contemplate that in the process of making coated granular compositions comprising a biologically active compound the thickness and/or homogeneity of a coating deposited on the granules of the granular composition e.g. as a result from applying a coating agent to the granules can be evaluated by recording sound signals arising from coated granules colliding with the granulator walls and subjecting the recorded vibration signals to computerized data processing.

Accordingly, the present invention provides in a first aspect a method for acoustic emission analysis of a granular composition comprising a biologically active compound, said method comprising colliding the granular composition with at least one surface transmitting low frequency vibrations, recording the low frequency vibration data arising from the collision, using at least one sound/vibration detecting sensor and subjecting the recorded low frequency vibration data to computerized data processing.

Further, in a second aspect, the invention provides a process for preparing granules comprising a biologically active compound and optionally auxiliary granulation agents in a granulation apparatus said process comprising the step of performing acoustic emission analysis in accordance with the first aspect of the invention (vide supra).

Still further, in a third aspect, the invention provides a granulation or coating apparatus comprising (a) a granulating or coating device comprising at least one chamber for granulating material or for coating of granulated material and at least one surface capable of transmitting low frequency sound, (b) at least one detector capable of detecting low frequency vibration, (c) means recording low frequency vibration signals detected by the detector and (d) means processing recording the low frequency vibration signals.

Finally, in a fourth aspect the invention encompasses use of acoustic emission analysis on granules comprising a biologically active compound. Said process is particularly useful in the granulation of enzymes.

BRIEF DESCRIPTION OF THE TABLES AND DRAWING

FIG. 1: Score plot obtained, from a Principal Component Analysis (PCA) when changing the supply of cellulose to a continuous high shear mixer granulation process.

FIG. 2: Score plot obtained from a Principal Component Regression (PCR) when changing the supply of cellulose to a continuous high shear mixer granulation process.

FIG. 3: Score plot obtained from a Partial Least Squares Regression (PLS) showing how granules with correct quality differ from granules not having correct quality.

FIG. 4: Line-plot showing how a PLS-model predicts the process condition.

FIG. 5: Line-plot showing how a PLS-model predicts the process condition.

DETAILED DESCRIPTION OF THE INVENTION

Acoustic Emission Analysis on Granules

The present invention relates, as described, to a method for performing acoustic emission analysis on a granular composition comprising an active compound. As a particle collides with a hard surface the particle will interfere with the surface and make the surface vibrate. The basic idea is that these vibrations give information on the characteristics of the particles. Accordingly, if the characteristics of the particles change the vibrations will also change.

The first step of the method comprises the colliding of the granular composition to be analyzed with a hard surface. In a granulation process the granules in a granulation apparatus will collide with each other and with the walls of the granulation chamber as long as movement is induced to granules.

The second step of the method comprises the recording of vibration caused by the collision between granules and the walls of the granulation apparatus. The vibration caused by the collision between granules and the walls of the granulation apparatus is recorded by vibration sensors sensitive to and capable of detecting sound and/or vibrations such as but not limited to piezoelectric sensors. In a particular embodiment one or more piezoelectric sensors such as accelerometers capable of detecting vibrations in the range of 10 Hz to less than 50 kHz, particularly 20 Hz to 20 kHz, more particularly 32 Hz to 25.6 kHz, more particularly 1 kHz to 15 kHz, more particularly 100 Hz to 10 kHz, even more particularly 500 Hz to 5 kHz are positioned directly on the wall of the granulation apparatus. In a particular embodiment at least one detected frequency is below 15 kHz.

The vibrating signals arising from collision between the granules and the walls of the granulation apparatus vary depending on placement of the vibration sensors. This means that the sensors may be placed anywhere they can detect vibration signals, depending on the granulation apparatus. In particular for a mixer apparatus we have found that placing one or more accelerometers close to inlet and/or outlet gives better results.

The one or more vibration sensors are connected to a computer unit capable of storing the recorded vibration data and/or capable of analyzing data on-line.

For analyzing the stored vibration data, these data are, in a particular embodiment, firstly subjected to Fast Fourier Transformation and then in a further particular embodiment an average spectrum is calculated, a so called Power Spectral Density (PSD) spectrum, to reduce noise. Subsequently, the transformed data are analyzed by a computer modeling system e.g. a chemometric method such as Principal Component Analysis (PCA), Partial Least Squares Regression (PLS), Principal Component Regression (PCR) or Multiple Linear Regression (MLR) or Neural Network (NN) (Barry J. Wythoff, Backpropagation neural networks; A tutorial, Chemometrics and Intelligent Laboratory Systems, Volume 18, Issue 2, February 1993, p. 115–155). This kind of data manipulation is long known to the art and standard software is commercially available for that purpose, such as The Unscrambler® from Camo, Norway. In this operation the data is modeled and e.g. rearranged into score plots. From the model it may be revealed if an unexpected change in a quality parameter of the granular composition has occurred during the granulation process.

The Granular Composition

Physical Properties

The granular composition of the invention is a composition comprising the biologically active compound and optionally auxiliary granulation agents and coating agents processed into particles or granules. Accordingly, finished granules are the result of the processes and methods of the invention. The term "granules" are to be understood as a predominantly spherical or near spherical structure of a macromolecular size, preferably having an average size measure in the longest diameter between 20–2000 μm, more preferably between 100–1000 μm, most preferably between 200–800 μm. The spherical granules preferably have a ratio, (a):(b), between the diameter in the shortest dimension (a) and the diameter in the longest dimension (b) of the granule of between 1:1 to 1:5, preferably between 1:1 to 1:3.

The "size distribution" of granules can be expressed in terms of the mass mean diameter of the individual particles. A mean mass diameter of D50 is the diameter at which 50% of the granules, by mass, have a smaller diameter, while 50% by mass have a larger diameter. The values D10 and D90 are the diameters at which 10% and 90%, respectively, of the granules, by mass, have a smaller diameter than the value in question. The "SPAN" indicates the breadth of the Particle size distribution and is expressed as: (D90-D10)/D50. For purposes of the present invention, the particle size distribution of granules after granulation is normally as narrow as possible. Use of acoustic emission analysis, in accordance with the present invention, for controlling the granulation process may aid in narrowing of the particle size distribution, and the SPAN of the granular composition after granulation is therefore particularly less than about 2.5, particularly less than about 2.0, more particularly less than about 1.5, and most particularly less than about 1.0.

The granules are in a particular embodiment coated with a coating agent, particularly those forming a homogenous, coherent and continuous, layer around the granules. The term coating agent as used herein is to be understood as single coating compound or a mixture of coating compounds. Coated granules thus consist of a granule core and a granule coating. Preferably the coating layer is relatively thick, in order to further reduce dusting and improve stability of the biologically active compound (see e.g. WO 01/25412). The coating thickness may be described by the ratio between the average diameter of a coated granule core and the average diameter of an uncoated granule core (hereinafter abbreviated $D_G/D_C$), i.e. the average diameter of the coated granule divided by the average diameter of the granule core only. If for example a granule core having a diameter of 100 µm is coated with a coating layer 200 µm thick, the granule would have a diameter of (200+100+200)=500 µm and $D_G/D_C$ is 500 µm/100 µm=5. Coated granules of the invention particularly have a $D_G/D_C$ of at least 1.1, which means that the thickness of the coating is at least 5% of the average granule core diameter. A more particular $D_G/D_C$ is at least 1.5, more particularly at least 2, more particularly at least 2.5, more particularly at least 3, most particularly at least 4. DG/DC is however particularly below about 100, particularly below about 50, more particularly below 25, and most particularly below 10. A most particular range for $D_G/D_C$ is about 4 to about 6.

Furthermore, in the present invention the coating is, in a particular embodiment substantially free of biologically active compound. The term "substantially free of biologically active compound" as used herein about a coating means that there is less than 5 mg of biologically active compound per gram coating agent.

Granulation

The term "granulation" is to be understood as building up larger solid granules from smaller particles and/or solids and/or dry matter contained in liquids. Hence, granulation requires binding together a number of small volume particles together to form particles having a greater volume and weight. As opposed hereto the process of compaction involves compressing particles of a starting volume and weight into particles of less volume, but the same weight. Compaction of granules may, if desired, be carried out after granulation if a smaller volume of granules is desired. In a particular embodiment the process of the invention is not a compaction process, but is selected from the group of Spray drying or spray cooling processes, mixer processes, layering processes, absorption processes and extrusion or pelletizing processes (vide infra).

The granulation process of the granules of the invention may be divided into the following non-exhaustive categories:
 a) Spray dried granules, wherein a liquid solution containing the biologically active compound is atomized in a spray dryer and form small droplets which during their way down the dryer dry to form a granular material comprising the active compound. Very small granules can be produced this way (Michael S. Showell (editor); *Powdered detergents*; Surfactant Science Series; 1998; vol. 71; page 140–142; Marcel Dekker). For these granules the active compound is intimately mixed with any other auxiliary granulation agents present in the liquid solution.
 b) Layered granules, wherein the biologically active compound is coated as a layer around a pre-formed core particle, wherein a solution containing the biologically active compound, and preferably auxiliary granulation agents, is atomized, typically in a fluid bed apparatus wherein the pre-formed core particles are fluidized, and the solution of active compound adheres to the core particles and dries up to leave a layer of dry biologically active compound on the surface of the core particle. Granules of a desired size can be obtained this way if a useful core particle of the desired size can be found. This type of granules is described in e.g. WO 97/23606
 c) Absorbed core granules, wherein rather than coating the biologically active compound as a layer around the core, the biologically active compound is absorbed onto and/or into the surface of the core. Such a process is described in WO 97/39116.
 d) Extruded or pelletized granules, wherein a paste containing the biologically active compound is pressed into granules in a mould or under pressure is extruded through a small opening and cut into granules which are subsequently dried. Such granules usually have a considerable size because of the material in which the extrusion opening is made (usually a plate with bore holes) sets a limit on the allowable pressure drop over the extrusion opening. Also, very high extrusion pressures when using a small opening increase heat generation in the paste, which may be harmful to the biologically active compound. (Michael S. Showell (editor); i Powdered detergents; Surfactant Science Series; 1998; vol. 71; page 140–142; Marcel Dekker)
 e) Spray cooled granules, wherein a powder of biologically active compound is suspended in molten wax and the suspension is sprayed, e.g. through a rotating disk atomizer, into a cooling chamber where the droplets quickly solidify (Michael S. Showell (editor); *Powdered detergents*; Surfactant Science Series; 1998; vol. 71; page 140–142; Marcel Dekker). For these granules the active compound is intimately mixed with the wax instead of being concentrated on its surface. Also U.S. Pat. Nos. 4,016,040 and 4,713,245 are documents relating to this technique
 f) High shear mixer granules, wherein a liquid containing the biologically active compound is added to a dry powder composition of auxiliary granulation agent. The liquid and the powder in a suitable proportion are mixed and as the moisture of the liquid is absorbed in the dry powder, the components of the dry powder will start to adhere and agglomerate and granules will build up, forming granules comprising the biologically active compound. For these granules the active compound is intimately mixed with the auxiliary granulation agents. Such a process is described in U.S. Pat. No. 4,106,991 (NOVO NORDISK) and related documents EP 170360 B1 (NOVO NORDISK), EP 304332 B1 (NOVO NORDISK), EP 304331 (NOVO NORDISK), WO 90/09440 (NOVO NORDISK) and WO 90/09428 (NOVO NORDISK).

Dust Particles in Granular Compositions

Dust particles, which may be present in a granular composition, may be characterized in that they are particles, which usually have a considerably smaller size than the granules and do not possess the characteristic spherical shape of the granules. Dust particles typically have an irregular non-spherical and abrupt structure such as rod or flake shaped. Dust particles are typically much smaller than the average size of granules, and most dust particles are, depending on the granular composition less than 20 µm in diameter. Accordingly, without being bound to the theory it is presently contemplated that these physical difference between granules and dust particles is contributing to the differences in low frequency sound arising when colliding the granules and dust particles with a surface.

Compounds in the Granular Composition
Biologically Active Compounds

The granular composition of the invention comprises a biologically active compound, preferably in a purified form. The term biologically active compound as used herein is to be understood as any compound, which is active in a biological system such as compounds, which interfere with and/or modifies biological pathways or biological reactions. The term "purified" as used herein is to be understood as biologically active compounds, which before granulation has been subjected to one or more purification step to remove e.g. excess material and/or undesired activities and/or to concentrate the active compound. In the case the active compound is prepared by a microbiological fermentation process purification preferably includes step selected from filtering, ultra-filtration, flocculation, sedimentation, evaporation, extraction and the like, to remove biomass and other undesired matter including water to yield a mixture which is enriched in the biologically active compound.

Biologically active compounds include among others organic compounds such as bio-catalysts, therapeutic agents, herbicides, pesticides and fungicides. Preferred biologically active compounds are producible by fermenting a microorganism producing the active compounds.

Preferred compounds are those among proteins and peptides, more preferably catalytic proteins, i.e. enzymes, because proteins such as enzymes are used in vast volumes in industry and are known to cause adverse allergy reactions in humans or animal when exposed to such proteins. Furthermore, enzymes are widely used in household products such as detergents for removing soil of a biological origin, and many industrial processes involves human handling of the enzymes. The enzyme may be any enzyme for which it is desired to separate the enzyme from the surrounding environment through granulation of the enzymes.

The enzyme classification employed in the present specification with claims is in accordance with *Recommendations* (1992) of the *Nomenclature Committee of the International Union of Biochemistry and Molecular Biology*, Academic Press, Inc., 1992.

Accordingly the types of enzymes which may appropriately be incorporated in granules of the invention include oxidoreductases (EC 1.-.-.-), transferases (EC 2.-.-.-), hydrolases (EC 3.-.-.-), lyases (EC 4.-.-.-), isomerases (EC 5.-.-.-) and ligases (EC 6.-.-.-).

Preferred oxidoreductases in the context of the invention are peroxidases (EC 1.11.1), laccases (EC 1.10.3.2) and glucose oxidases (EC 1.1.3.4)], while preferred transferases are transferases in any of the following sub-classes:

a) Transferases transferring one-carbon groups (EC 2.1);
 b) Transferases transferring aldehyde or ketone residues (EC 2.2); acyltransferases (EC 2.3);
 c) Glycosyltransferases (EC 2.4);
 d) Transferases transferring alkyl or aryl groups, other that methyl groups (EC 2.5); and
 e) Transferases transferring nitrogenous groups (EC 2.6).

A most preferred type of transferase in the context of the invention is a transglutaminase (protein-glutamine γ-glutamyltransferase; EC 2.3.2.13).

Further examples of suitable transglutaminases are described in WO 96/06931 (Novo Nordisk A/S).

Preferred hydrolases in the context of the invention are: Carboxylic ester hydrolases (EC 3.1.1.-) such as lipases (EC 3.1.1.3); phytases (EC 3.1.3.-), e.g. 3-phytases (EC 3.1.3.8) and 6-phytases (EC 3.1.3.26); glycosidases (EC 3.2, which fall within a group denoted herein as "carbohydrases"), such as α-amylases (EC 3.2.1.1); peptidases (EC 3.4, also known as proteases); and other carbonyl hydrolases].

In the present context, the term "carbohydrase" is used to denote not only enzymes capable of breaking down carbohydrate chains (e.g. starches) of especially five- and six-membered ring structures (i.e.glycosidases, EC 3.2), but also enzymes capable of isomerizing carbohydrates, e.g. six-membered ring structures such as D-glucose to five-membered ring structures such as D-fructose.

Carbohydrases of relevance include the following (EC numbers in parentheses): α-amylases (3.2.1.1), β-amylases (3.2.1.2), glucan 1,4-α-glucosidases (3.2.1.3), cellulases (3.2.1.4), endo-1,3(4)-β-glucanases (3.2.1.6), endo-1,4-β-xylanases (3.2.1.8), dextranases (3.2.1.11), chitinases (3.2.1.14), polygalacturonases (3.2.1.15), lysozymes (3.2.1.17), β-glucosidases (3.2.1.21), α-galactosidases (3.2.1.22), β-galactosidases (3.2.1.23), amylo-1,6-glucosidases (3.2.1.33), xylan 1,4-β-xylosidases (3.2.1.37), glucan endo-1,3-β-D-glucosidases (3.2.1.39), α-dextrin endo-1,6-α-glucosidases (3.2.1.41), sucrose α-glucosidases (3.2.1.48), glucan endo-1,3-α-glucosidases (3.2.1.59), glucan 1,4-β-glucosidases (3.2.1.74), glucan endo-1,6-β-glucosidases (3.2.1.75), arabinan endo-1,5-α-L-arabinosidases (3.2.1.99), lactases (3.2.1.108), chitosanases (3.2.1.132) and xylose isomerases (5.3.1.5).

Examples of commercially available oxidoreductases (EC 1.-.-.-) include Gluzyme™ (enzyme available from Novozymes A/S. Examples of commercially available proteases (peptidases) include Kannase™, Everlase™, Esperase™, Alcalase™, Neutrase™, Durazym™, Savinase™, Pyrase™, Pancreatic Trypsin NOVO (PTN), Bio-Feed™ Pro and Clear-Lens™ Pro (all available from Novozymes A/S, Bagsvaerd, Denmark).

Other commercially available proteases include Maxatase™, Maxacal™, Maxapem™, Opticlean™ and Purafect™ (available from Genencor International Inc. or Gist-Brocades).

Examples of commercially available lipases include Lipoprime™ Lipolase™, Lipolase™ Ultra, Lipozyme™, Palatase™, Novozym™ 435 and Lecitase™ (all available from Novozymes A/S.

Other commercially available lipases include Lumafast™ (*Pseudomonas mendocina* lipase from Genencor International Inc.); Lipomax™ (*Ps. pseudoalcali* genes lipase from Gist-Brocades/Genencor Int. Inc.; and Bacillus sp. lipase from Solvay enzymes.

Examples of commercially available carbohydrases include Alpha-Gal™, Bio-Feed™ Alpha, Bio-Feed™ Beta, Bio-Feed™ Plus, Bio-Feed™ Plus, Novozyme™ 188, Celluclast™, Cellusoft™, Ceremyl™, Citrozym™, Denimax™, Dezyme™, Dextrozyme™, Finizym™, Fungamyl™, Gamanase™, Glucanex™, Lactozym™, Maltogenase™, Pentopan™, Pectinex™, Promozyme™, Pulpzyme™, Novamyl™, Termamyl™, AMG™ (Amyloglucosidase Novo), Maltogenase™, Sweetzyme™ and Aquazym™ (all available from Novozymes A/S)

The amount of enzyme to be incorporated in a granule of the invention will depend on the intended use of the granule. For many applications, the enzyme content will be as high as possible or practicable.

The content of active compound, in particular enzyme (calculated as pure enzyme protein) in a granule of the invention will typically be in the range of from about 0.5% to 50% by weight of the granule. In some embodiments it may be desired to incorporate even higher amounts of active compound into the granules, such as 50–100%, particularly 50–90%, more particularly 60–80%.

Auxiliary Granulation Agents

The granules of the invention preferably contains auxiliary granulation agents for purposes such as aiding the formation of granules, controlling density and volume of granules, controlling amount of active compound in the granules, stabilizing the active compound and the like.

Auxiliary granulating agents may include but is not limited to:

a) Fillers such as fillers conventionally used in the field of granulation e.g. water soluble and/or insoluble inorganic salts such as finely ground alkali or earth alkali salts of sulphate, carbonate and/or chloride), clays such as kaolin (e.g. Speswhite™, English China Clay), bentonites, talcs, zeolites, and/or silicates.

b) Binders such as binders conventionally used in the field of granulation e.g. binders with a high melting point or no melting point at all and of a non waxy nature e.g. polyvinyl pyrrolidon, dextrins, polyvinylalkohol, cellulose derivatives, for example hydroxypropyl cellulose, methyl cellulose or CMC. A suitable binder is a carbohydrate binder such as Glucidex 21D available from Roquette Freres, France.

c) Fiber materials such as fibers conventionally used in the field of granulation. Pure or impure cellulose in fibrous form can be sawdust, pure fibrous cellulose, cotton, or other forms of pure or impure fibrous cellulose. Also, filter aids based on fibrous cellulose can be used. Several brands of cellulose in fibrous form are on the market, e.g. CEPO and ARBOCELL. In a publication from Svenska Tramjolsfabrikerna AB, "Cepo Cellulose Powder" it is stated that for Cepo S/20 cellulose the approximate maximum fiber length is 500 μm, the approximate average fiber length is 160 μm, the approximate maximum fiber width is 50 μm and the approximate average fiber width is 30 μm. Also, it is stated that CEPO SS/200 cellulose has an approximate maximum fiber length of 150 μm, an approximate average fiber length of 50 μm, an approximate maximum fiber width of 45 μm and an approximate average fiber width of 25 μm. Cellulose fibers with these dimensions are very well suited for the purpose of the invention. The words "Cepo" and "Arbocel" are Trademarks. Preferred fibrous cellulose is Arbocel™ BFC200. Also synthetic fibers may be used as described in EP 304331 B1 and typical fibers may be made of polyethylene, polypropylene, polyester, especially nylon, polyvinylformat, poly(meth)acrylic compounds.

d) Liquid agents such as conventionally used in the field of granulation. A liquid agent is used in conventional mixer granulation processes for enabling the build up or agglomeration of the conventional granulating component particles into granules. The liquid agent is water and/or a waxy substance. The liquid agent is always used in a liquid phase in the granulation process but may later on solidify; the waxy substance if present, therefore, is either dissolved or dispersed in the water or melted. By the term "waxy substance" as used herein is meant a substance which possesses all of the following characteristics 1) the melting point is between 30 and 100° C., preferably between 40 and 60° C., 2) the substance is of a tough and not brittle nature, and 3) the substance possesses a certain plasticity at room temperature. Both water and waxy substance are liquid agents, i.e. they are both active during the formation of the granules; the waxy substance stays as a constituent in the finished granules, whereas the majority of the water is removed during a drying step. Examples of waxy substances are polyglycols, fatty alcohols, ethoxylated fatty alcohols, mono-, di- and triglycerolesters of higher fatty, acids, e.g. glycerol monostearate, alkylarylethoxylates, and coconut monoethanolamide.

If a high amount of waxy substance is used, relatively little water should be added, and vice versa. Thus, the liquid agent can be either water alone, waxy substance alone or a mixture of water and waxy substance. When a mixture of water and waxy substance is used the water and the waxy substance can be added in any sequence, e.g. first the water and then the waxy substance, or first the waxy substance and then the water or a solution or suspension of the waxy substance in the water. Also, when a mixture of water and waxy substance is used, the waxy substance can be soluble or insoluble (but dispersible) in water. If water is used a liquid agent it may not be a part of the finished mixer granule as usually most of the water is dried off at a subsequent drying of the mixer granules.

e) Enzyme stabilizing or protective agents such as conventionally used in the field of granulation. Stabilizing or protective agents may fall into several categories: alkaline or neutral materials, reducing agents, antioxidants and/or salts of first transition series metal ions. Each of these may be used in conjunction with other protective agents of the same or different categories. Examples of alkaline protective agents are alkali metal silicates, -carbonates or bicarbonates, which provide a chemical scavenging effect by actively neutralizing e.g. oxidants. Examples of reducing protective agents are salts of sulfite, thiosulfite or thiosulfate, while examples of antioxidants are methionine, butylated hydroxytoluene (BHT) or butylated hydroxyanisol (BHA). Most preferred agents are salts of thiosulfates, e.g. sodium thiosulfate. Also enzyme stabilizers may be borates, borax, formates, di- and tricarboxylic acids and reversible enzyme inhibitors such as organic compounds with sulfhydryl groups or alkylated or arylated boric acids.

f) Cross-linking agents such as conventionally used in the field of granulation. Cross-linking agents may be enzyme-compatible surfactants e.g. ethoxylated alcohols, especially ones with 10 to 80 ethoxy groups.

Further, suspension agents, mediators (for boosting bleach action upon dissolution of the granule in e.g. a washing application or mediators for enzymes) and/or solvents may be incorporated as auxiliary granulating agents.

Coating Agents

The coating comprises one or more conventional coating agent components such as described in WO 89/08694, WO 89/08695, EP 270 608 B1 and/or WO 00/01793. Other examples of coating agents may be found in U.S. Pat. No. 4,106,991, EP 170360, EP 304332, EP 304331, EP 458849, EP 458845, WO 97/39116, WO 92/12645A, WO 89/08695, WO 89/08694, WO 87/07292, WO 91/06638, WO 92/13030, WO 93/07260, WO 93/07263, WO 96/38527, WO 96/16151, WO 97/23606, U.S. Pat. Nos. 5,324,649, 4,689,297, EP 206417, EP 193829, DE 4344215, DE 4322229 A, DD 263790, JP 61162185 A and/or JP 58179492. Especially the salt coatings described in WO 00/01793 are useful for coatings in the present invention.

The coating agent may be selected from the list of auxiliary granulation agents described, supra. Further coating agents may be selected the following non-limiting list of polymers, chlorine scavengers, plasticizers, pigments, lubricants (such as surfactants or antistatic agents) and fragrances.

Polymers useful in coating layers include vinyl polymers or vinyl co-polymers such as polyvinyl alcohol (PVA) and/or polyvinyl pyrrolidone or derivatives thereof. Also included are isophtalic acid polymers and polyethylene glycols (PEGs) (see e.g. WO 01/25412 and U.S. Pat. No. 4,106,991 ex. 22).

Plasticizers useful in coating layers in the context of the present invention include, for example: polyols such as sugars, sugar alcohols, or polyethylene glycols (PEGS) having a molecular weight less than 1000; urea, phthalate esters such as dibutyl or dimethyl phthalate; and water.

Suitable pigments include, but are not limited to, finely divided whiteners, such as titanium dioxide or kaolin, coloured pigments, water soluble colorants, as well as combinations of one or more pigments and water soluble colorants.

As used in the present context, the term "lubricant" refers to any agent, which reduces surface friction, lubricates the surface of the granule, decreases tendency to build-up of static electricity, and/or reduces friability of the granules. Lubricants can also play a related role in improving the coating process, by reducing the tackiness of binders in the coating. Thus, lubricants can serve as anti-agglomeration agents and wetting agents. Examples of suitable lubricants are polyethylene glycols (PEGs) and ethoxylated fatty alcohols.

In embodiments aimed primarily at granules for detergent formulations, different "functional" components could be added to the coating such as TAED, CMC, bleach, OBA, surfactants, perfume as well as other functional components used in detergent formulations known to the person skilled in the art. The coating may also optionally comprise functional components selected for their specific use in the, pharmaceutical industry, agriculture, foodstuffs industry, baking industry, additives industry, feed industry, detergents industry or other industries where granules comprising a biologically active compound can be used.

In a preferred embodiment of the invention the granule of the invention is coated with a protective coating having a high constant humidity of at least 81% such as described in WO 00/01793, which is hereby incorporated by reference. One such coating is a coating containing predominantly sodium sulfate. Accordingly, the coating should, in particular embodiments, act as moisture and/or bleach barrier to stabilize the biologically active compound in the core. Furthermore, in further embodiments the coating acts as a mechanical barrier during mechanical processes such as dosing or tabletting or pelletizing. In particular embodiments, the coating is sufficiently compressible and flexible for the core to withstand a tabletting or pelletizing process, both in a structural sense and with regard to the stability of the activity of the active compound. This is potentially most applicable for detergent formulations and animal feed.

Acoustic Emission Analysis in Granulation and Coating Processes

The present invention also encompass processes for preparing granular compositions comprising an active compound and optionally auxiliary granulation agents in a granulation apparatus using the above mentioned method of acoustic emission analysis to predict properties of the granular composition and control and improve the preparation process.

Accordingly, the present invention provides a process for preparing granules comprising an active compound, particularly compounds being biologically active, and optionally auxiliary granulation agents in a granulation apparatus said process comprising the step of performing acoustic emission analysis on the granular composition as described, supra, on the granules forming in the granulation apparatus.

In a particular embodiment the acoustic emission analysis is carried out during the formation of granules in the granulation process, in particular on-line, meaning that the acoustic emission analysis is performed more than one time in real time during the granulation process with a suitable rate of repetition. The repetition rate will, inter alia, depend on the data processing of data from the detector(s). In the preferred embodiment of using a vibration sensor about several recordings per second is recorded. The term "formation of granules" includes also coating granules with a coating layer. In this embodiment the process also preferably comprises the step of changing at least one process parameter as a result of the acoustic emission analysis. The process parameter to be changed may be any parameter influencing the granulation process and/or the properties of the formed granules. These parameters may be the supply of granulation material, i.e. active compound and/or auxiliary granulation agents and/or coating agent to the granulator, supply of gas to the granulator, slide valve position, holding time, temperature in the granulator, pressure in the granulator, pH in the granulator, mixer speed and mechanical force conferred to the granulation material. The process parameter may be changed manually or through an automated control system connected to the granulation apparatus.

In a further additional embodiment acoustic emission analysis in accordance with the invention may also suitably be used to control dusting properties of finished granular compositions after granulation. Accordingly, the invention further provides a method for acoustic emission analysis of dust in a granular composition comprising an active compound. Using this method, granular compositions, which do not meet the desired quality with respect to dust, may be discarded or reprocessed.

In a further additional embodiment acoustic emission analysis in accordance with the invention may also suitably be used to control coating thickness and/or homogeneity of finished granular compositions after granulation. Accordingly, the invention further provides a method for acoustic emission analysis of coating thickness in a composition of coated granules comprising an active compound. Using this method granular compositions, which do not meet the desired quality with respect to coating thickness be discarded or reprocessed.

Granulation Apparatus

Also included in the scope of the invention is a granulation and/or coating apparatus comprising means for performing acoustic emission analysis on granular compositions in accordance with the invention. Accordingly, the invention provides a granulation or coating apparatus comprising:

(a) a granulation or coating device comprising at least one chamber for processing material into granules or coated granules and at least one surface transmitting low frequency sound (b) an arrangement for performing acoustic emission analysis comprising at least one vibration sensor capable of detecting sound and/or vibrations in the aforementioned frequencies and optionally amplifying and filtering units and a computer unit.

The granulation or coating device may be any conventional granulation device is preferably selected from fluid bed granulators or coaters, high shear mixer granulators, coating mixers, spray dryers, a spray coolers and extruders.

As indicated above the arrangement for performing acoustic emission analysis is suitably connected to the granulation or coating device to enable on-line or at-line acoustic emission analysis of granular compositions. On-line analysis is to be understood as analysis performed on granules as they are actually being granulated, e.g. by analyzing granules in the granulator or in a recycled purge stream. At-line analysis is to be understood as analysis performed down stream after the granulation process (e.g. at the outlet) or on non-recycled samples taken from the granulator during granulation.

The granulation apparatus may comprise other elements such as computing units for processing data from sensors, optionally equipped with specialized data handling hardware and software.

The granulation apparatus may also comprise control units linked to the computing units for controlling and adjusting the granulation process based on the results of the acoustic emission analysis. A control unit may be a PC, PLC or other equipment capable of receiving data from a computing unit and producing/converting these data into output controlling one or more hardware devices influencing the granulation process, such as feed streams, speed, temperature, airflows etc.

The procedure for carrying out the present is demonstrated in the following experiments. The experiments are only examples on embodiments of the invention and should in no way be interpreted as limiting to the scope of the invention.

EXAMPLES

Equipment used in the examples:

| Equipment | Vendor | Product |
|---|---|---|
| Digital recorder | SONY | type PC216A |
| Digital recorder | HHB | type PDR1000 |
| Accelerometer | Endevco | type 2258A |
| Accelerometer | Brüel & Kjær | type 4502/4503 |
| Accelerometer | Brüel & Kjær | type 7259A-100 |
| Data recording system | Difa | type Scadas |
| Data recording system | Brüel & Kjær | Portable Pulse Type 3560 C: Type 2827, 3032A and 7533 |
| Primary | | |
| Signal treatment software | Brüel & Kjær | Type 7700B, version 5 |
| Signal treatment software | LMS | Cada-X, TMON |
| Secondary | | |
| Signal treatment software | Camo ASA | The Unscrambler, version 7.6 and 7.6 SR-1 |

Example 1

Effects of changing amount of fiber material in a granulation process as measured with acoustic emission analysis.

Figure 1:
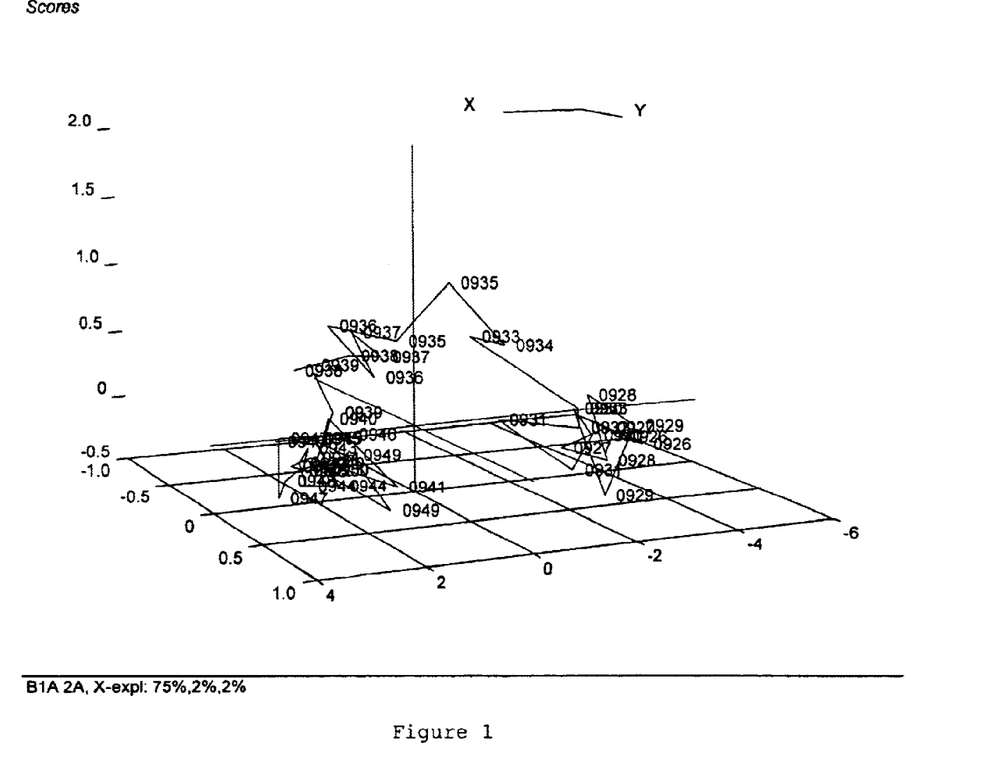

In continuous high shear mixer granulation process the amount of cellulose fiber supplied to the granulation process was changed at a given time. The granulator was mounted with an accelerometer for detection of vibrations. The accelerometer was placed on the interconnecting section between two mixers placed in series. The vibrations from 43 Hz to 25 kHz were recorded during the change of fiber supply and the recorded data were first treated with FFT (Fast Fourier Transformation). The FFT analysis was performed (according to the vendors manual) with 512 lines with Hanning window and 50% overlap. All FFT spectra obtained in 5 seconds (500 spectra) were linearly averaged to Power Spectral Density (PSD) (according to the vendors manual) every 30 seconds to remove noise. Subsequently the data was processed using Principal Component Analysis (PCA) and a score plot was generated as depicted in FIG. 1. From the score plot it can be seen that a change in vibration occurs upon changing the amount of cellulose fiber supplied to the process.

Acoustic data was detected by an accelerometer type 2258A and recorded by a digital recorder from HHB using data recording system Difa.

FFT and PSD were performed using the standard software Cada-X TMON from LMS.

PCA was performed using The Unscrambler®, version 7.6. The PCA algorithm is described in The Unscrambler User Manual, Camo ASA, 1998. Basic chemometric theory e.g. PCA and score plots are given in Martens H., Næs, T., Multivariate calibration, 2. ed., Wiley, New York, 1993 and Esbensen, K. et. al., Multivariate Analysis in practice, 3. ed., Camo ASA, Trondheim, 1998.

Example 2

Positioning Accelerometers

In this example the effect of different positioning of accelerometers were tested when changing the amount of binder to a continuous granulation process. 4 accelerometers were placed close to each other on the same horizontal line on a high shear mixer granulator and this configuration was expected to give only small time delays between the accelerometers. This was not the case. The first accelerometer on the line detected a change in binder as expected while the second, third and fourth accelerometer did not detect the change at all or detected the change very poorly. This shows that the placement of the accelerometers is important when using acoustic emission for detecting changes in granulate characteristics. Same equipment as in example 1 was used except the accelerometers were type 4502/4503 from Brüel & Kjær.

Example 3

Small and Large Granules

In this example the amount of cellulose was increased from an average of 8.5% to an average of 11%. The change in amount of cellulose results in a decrease in particle size.

The accelerometer was placed mid on the rear side of the mixer granulator.

Figure 2:
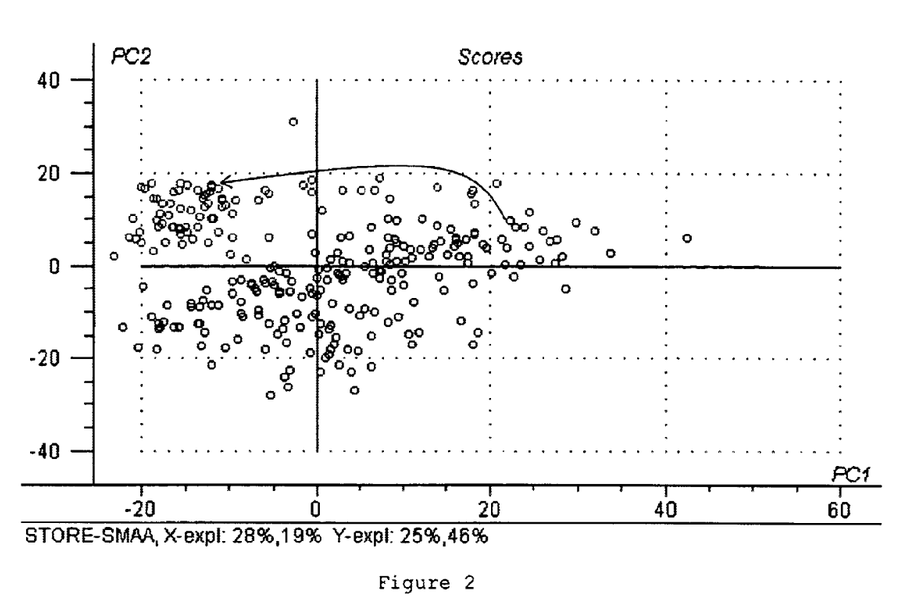

The vibrations from 32 Hz to 25.6 kHz were recorded during the process and treated with FFT (Fast Fourier Transformation). The FFT analysis was performed with 800 lines with Hanning window and 50% overlap. All FFT spectra obtained in 1.5 seconds (95 spectra) was exponentially averaged to Power Spectral Density (PSD) every 60 second to remove noise. Subsequently the data was processed using Principal component regression (PCR) and a score plot was generated as depicted in FIG. 2. One dot in the score plot represents a PSD spectrum. The PCR was carried out with the PSD spectra as x-data and a classification variable identifying PSD spectra to be related to small and large granules as Y-data. The score plot revealed that the recorded data changed as a result of the increasing addition of cellulose to the granulation process. In the score plot the arrow indicates how the recorded acoustic signals gradually changed simultaneously with the change in the characteristics of the granules, the granules gradually changed from normal size particles (black dots) to smaller size particles (grey dots).

Acoustic data was collected with an accelerometer type 7259A-100 using the data recording system Potable PULSE from Brüel & Kjær.

FFT and PSD were performed by the software Portable PULSE as described in the help file to the software PULSE, type 7700B version 5 from Brüel & Kjær.

PCR was performed with The Unscrambler®. The PCR algorithm is described in The Unscrambler User Manual, Camo ASA, 1998. Basic chemometric theory e.g. PCR and score plots are given in Martens H., Næs, T., Multivariate calibration, 2. ed., Wiley, New York, 1993 and Esbensen, K. et. al., Multivariate Analysis in practice, 3. ed., Camo ASA, Trondheim, 1998.

From this example it is clear that small particles in a granulation process such as dust may be predicted using the method of the invention.

Example 4

A granulation process was put under different changes in process conditions. An experienced process technician evaluated the quality of the different granules subjectively and separated the granules into granules which had the correct quality and granules which did not have the correct quality. The accelerometer was placed at the bottom on the rear side at the inlet of the mixer granulator.

Figure 3:
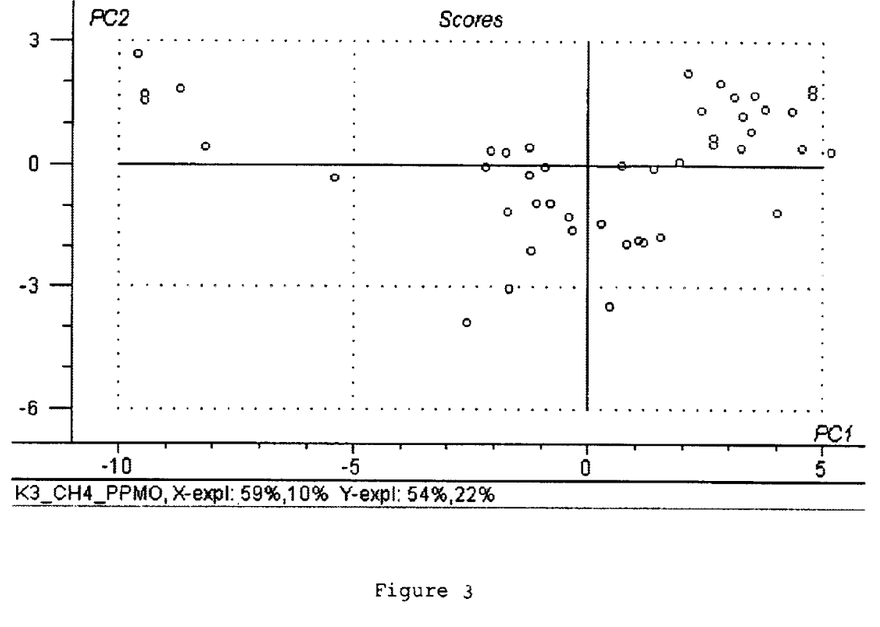

The vibrations from 32 Hz to 25.6 kHz were recorded during the process and treated with FFT (Fast Fourier Transformation). The FFT analysis was performed with 800 lines with Hanning window and 50% overlap. All FFT spectra obtained in 1.5 seconds (95 spectra) were exponentially averaged to Power Spectral Density (PSD) every 120 second to remove noise. Subsequently the data was processed using Principal Least Squares regression (PLS) and a score plot was generated as depicted in FIG. 3. The PLS was carried out with the PSD spectra as X-data and a classification variable identifying PSD spectra to be related to whether or not the granules had the correct quality (1) or not (0) as Y-data. Granules, which were found of correct quality by the technician, was found in the score plot as one distinct group (see FIG. 3) as grey dots, and granules, which did not have the correct quality, was found in a different distinct group as black dots. These results emphasized that the method of the present invention is indeed highly useful as a tool for predicting the quality of enzyme-containing granules in their making.

Acoustic data was collected with an accelerometer type 7259A-100 using the data recording system Portable PULSE from Brüel & Kjær. FFT and PSD were performed by the software Portable PULSE as described in the help file to the software PULSE, type 7700B version 5 from Brüel & Kjær.

PLS was performed with The Unscrambler®, version 7.6 SR-1. The PLS algorithm is described in The Unscrambler User Manual, Camo ASA, 1998. Basic chemometric theory e.g. PLS and score plots are given in Martens H., Næs, T., Multivariate calibration, 2. ed., Wiley, New York, 1993 and Esbensen, K. et. al., Multivariate Analysis in practice, 3. ed., Camo ASA, Trondheim, 1998.

Example 5

Classification of the State of the Granulation Process 4 accelerometers were placed at the outlet of a mixer granulator, 1 accelerometer was placed between inlet and outlet on the mixer and 1 accelerometer was placed at the inlet. The vibrations from 32 Hz to 25.6 kHz were recorded during the process and treated with FFT (Fast Fourier Transformation). The FFT analysis was performed with 800 lines with Hanning window and 50% overlap. All FFT spectra obtained in 1.5 seconds (95 spectra) was exponentially averaged to Power Spectral Density (PSD) every 60 second to reduce noise.

The PSD spectra were used for PLS-modeling, to model the relation between changes in the acoustic vibrations and the process conditions.

The process condition was evaluated by a process technician and is described in two ways:

A. The process condition got the value 1 when the granules were in order, and no process changes were needed, and the process condition got the value −1 when the granules were not in order and process changes were required to get the granules in order.

B. As above 1/−1 when the granules were strictly in order/not in order, 0.5/−0.5 when the granules were slightly out of order/slightly not in order.

The acoustic signals were monitored as described above every minute but the process technician's evaluation came with variable intervals.

The models were based on the acoustic signals (PSD spectra) as X-data and the respective observations from the process technician, were given numerical values as described in A and B as Y-data.

Figure 4:
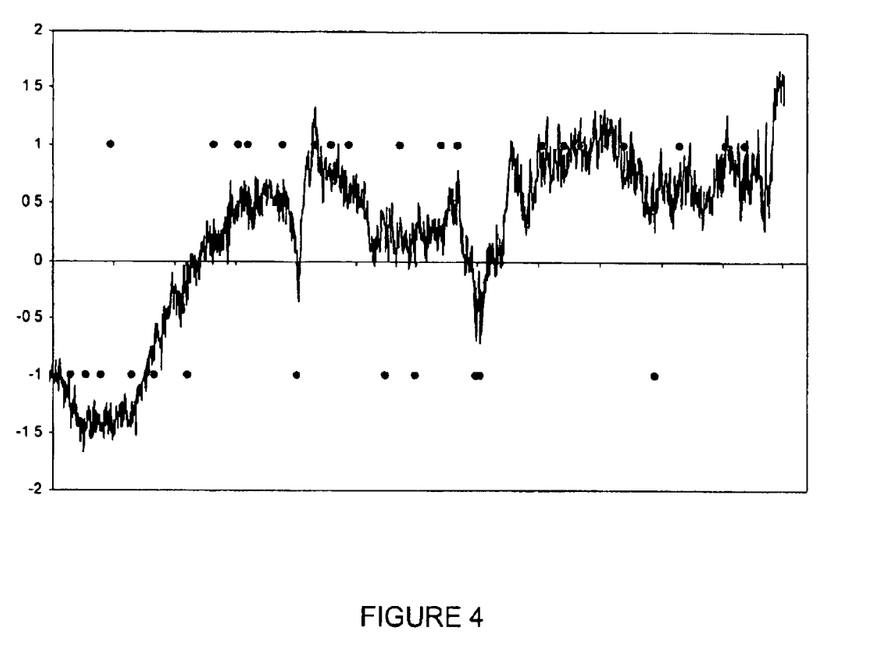
Figure 5:
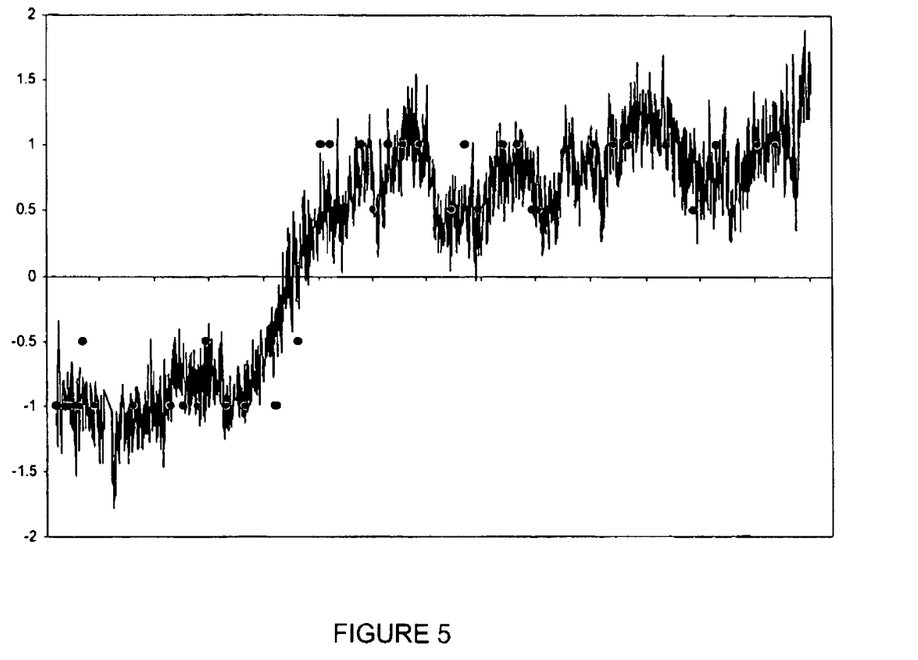

FIG. 4 show how the PLS model between the acoustic signals and the process condition as described in A, predicts the process technician's evaluation of the granules and the quality of the prediction. The black continuous curve is the condition of the process (in order/not in order) as predicted by the model based on the acoustic signals and the grey dots are the technician's actual evaluation of the granules. FIG. 5 show how the PLS model between the acoustic signals and the process condition as described in B, predicts the process technician's evaluation of the granules and the quality of this prediction.

In FIGS. 4 and 5 the Y-axis give information about the process state. The X-axis is the time-scale covering approx. 40 hours. The prediction based on the acoustic signals (black curve) correlates well to the process technician's evaluation (grey dots).

Acoustic data was collected with accelerometers type 7259A-100 using the data recording system Portable PULSE from Brüel & Kjær. FFT and PSD were performed by the software Portable PULSE as described in the help file to the software PULSE, type 7700B version 5 from Brüel & Kjær.

PLS modeling and prediction was performed with The Unscrambler, version 7.6 SR-1. The PLS algorithm is described in The Unscrambler User Manual, Camo ASA, 1998.

Following variable selection methods were performing the PLS-modelling: "Jack Knife", described in The Unscrambler version 7.6 SR-1 help file and user manual (The Unscrambler User Manual, Camo ASA, 1998), and "Principal Variables with All Possible Combinations", L. Munck, L. Nørgaard, S. B. Engelsen, R. Bro and C. A. Anderson, C Chemometrics in food science-a demonstration of the feasibility of a highly exploratory, inductive evaluation strategy of fundamental scientific significance, Chemometrics and Intelligent Laboratory Systems, Volume 44, Issues 1–2, 14 December 1998, p. 31–60.)

What is claimed is:

1. A method for acoustic emission analysis of a non-compacted granular composition comprising a biologically active compound, said method comprising colliding the non-compacted granular composition with at least one surface, recording low frequency vibration data in the range of 10 Hz to less than 50 kHz, arising from the collision, with at least one vibration detecting sensor and subjecting the recorded low frequency vibration data to computerized data processing.

2. The method according to claim 1, wherein the low frequency vibrations has a frequency between 32 Hz to 25.6 kHz.

3. The method according to claim 1, wherein at least one of the low frequency vibrations is a frequency below 15 kHz.

4. The method according to claim 1, wherein the vibration detecting sensor is a piezo-electric sensor.

5. The method according to claim 1, wherein the vibration detecting sensor is an accelerometer.

6. The method according to claim 1, wherein the data processing is selected form the group of Fast Fourier Transformation, Power Spectral Density, Principal Component Analysis, Partial Least Squares Regression, Principal Component Regression, Multiple Linear Regression, Neural Network or a combination thereof.

7. The method according to anyone of claims 1–6, wherein the biologically active compound is in a purified form.

8. The method according to claim 1, wherein the biologically active compound is selected from bio-catalysts, therapeutic agents, herbicides, pesticides and fungicides.

9. The method according to claim 8, wherein the biologically active compound is selected from proteins and peptides.

10. The method according to claim 9, wherein the biologically active compound is an enzyme.

11. The method according to claim 1, wherein the granular composition further comprises auxiliary granulation agents.

12. The method according to claim 11, wherein the auxiliary granulation agents are selected from fibre materials, binders, fillers, liquid agents, enzyme stabilizers, suspension agents, cross linking agents, mediators and/or solvents.

13. The method according to claim 1, wherein the granules of the granular composition comprises a core wherein the biologically active compound is intimately mixed with auxiliary granulation agents.

14. The method according to claim 1, wherein the granules of the granular composition comprise a core particle coated with a layer comprising the biologically active compound.

15. The method according to claim 1, wherein the granules of the granular composition have an average size between 20–2000 μm.

16. The method according to claim 1, wherein the granules of the granular composition are coated with a coating agent.

17. The method of claim 1, wherein the acoustic emission analysis of the non-compacted granular composition is performed as a step of a granulation process used for forming the non-compacted granular composition.

18. The process of claim 17, and wherein the acoustic emission analysis of the non-compacted granular composition is performed on-line and in real time during the granulation process and is repeated more than one time during the granulation process.

19. The method of claim 17, further comprising the step of changing at least one process parameter of the granulation process as a result of the acoustic emission analysis.

* * * * *